(12) United States Patent
Mase

(10) Patent No.: US 6,532,399 B2
(45) Date of Patent: Mar. 11, 2003

(54) DISPENSING METHOD USING INDIRECT COUPLING

(75) Inventor: Joseph C. Mase, Chicago, IL (US)

(73) Assignee: Baxter International Inc., Deerfield, IL (US)

(*) Notice: Subject to any disclaimer, the term of this patent is extended or adjusted under 35 U.S.C. 154(b) by 0 days.

(21) Appl. No.: 09/874,755

(22) Filed: Jun. 5, 2001

(65) Prior Publication Data

US 2002/0179622 A1 Dec. 5, 2002

(51) Int. Cl.[7] .............................................. G06F 17/00
(52) U.S. Cl. ....................... 700/237; 700/236; 700/242; 700/244; 70/85; 70/264; 70/266; 70/277; 70/280; 221/15 OR; 221/154; 312/215; 312/333
(58) Field of Search ................................. 700/231, 232, 700/237, 241, 242, 236, 244; 221/154, 15 OR; 312/215, 333; 70/85, 264, 266, 277, 280

(56) References Cited

U.S. PATENT DOCUMENTS

| | | |
|---|---|---|
| 3,556,342 A | 1/1971 | Guarr |
| 3,715,148 A | 2/1973 | Beals |
| 3,744,867 A | 7/1973 | Shaw |
| 3,762,601 A | 10/1973 | McLaughlin |
| 3,917,045 A | 11/1975 | Williams et al. |
| 3,998,356 A | 12/1976 | Christensen |
| 4,019,793 A | 4/1977 | Gerding |
| 4,071,747 A | 1/1978 | Pantenella |
| 4,114,965 A | 9/1978 | Oye et al. |
| 4,179,724 A | 12/1979 | Bonhomme |
| 4,209,211 A | 6/1980 | Alford |
| 4,267,942 A | 5/1981 | Wick, Jr. et al. |
| 4,360,125 A | 11/1982 | Martindale et al. |
| 4,382,688 A | 5/1983 | Machamer |
| 4,473,884 A | 9/1984 | Behl |
| 4,546,901 A | 10/1985 | Buttarazzi |
| 4,575,719 A | 3/1986 | Bertagna et al. |
| 4,626,105 A | 12/1986 | Miller |
| 4,635,053 A | 1/1987 | Banks et al. |
| 4,640,560 A | 2/1987 | Blum |
| 4,681,504 A | 7/1987 | Welch, Sr. |
| 4,691,470 A | 9/1987 | Landell et al. |
| 4,695,594 A | 9/1987 | Pressman |
| 4,717,042 A | 1/1988 | McLaughlin |
| 4,737,910 A | 4/1988 | Kimbrow |
| 4,783,740 A | 11/1988 | Ishizawa et al. |
| 4,785,969 A | 11/1988 | McLaughlin |
| 4,803,604 A | 2/1989 | Nichols et al. |
| 4,811,764 A | 3/1989 | McLaughlin |
| 4,813,753 A | 3/1989 | Relyea |
| 4,847,764 A | 7/1989 | Halvorson |
| 4,866,661 A | 9/1989 | de Prins |
| 4,942,275 A | 7/1990 | Addey et al. |
| 4,962,491 A | 10/1990 | Schaeffer |
| 4,967,928 A | 11/1990 | Carter |

(List continued on next page.)

FOREIGN PATENT DOCUMENTS

FR 2 760 557 A1 5/1997

OTHER PUBLICATIONS

International Search Report ("ISR"), and the "Notification of Transmittal of the International Search Report or the Declaration," issued by the European Patent Office as the International Searching Authority and pertaining to International Application PCT/US02/21239 having an International filing date of Jun. 3, 2002, and naming Baxter International Inc. as the Applicant.

*Primary Examiner*—Khoi H. Tran
(74) *Attorney, Agent, or Firm*—Mark J. Buonaiuto; Steve Auten

(57) ABSTRACT

The present invention provides a novel method for selectively dispensing inventoried items, such as pharmaceutical and therapeutic agents in a hospital.

16 Claims, 1 Drawing Sheet

U.S. PATENT DOCUMENTS

| | | | |
|---|---|---|---|
| 5,014,875 A | | 5/1991 | McLaughlin et al. |
| 5,047,948 A | | 9/1991 | Turner |
| 5,055,660 A | | 10/1991 | Bertagna |
| 5,069,511 A | | 12/1991 | Swets et al. |
| 5,200,891 A | | 4/1993 | Kehr et al. |
| 5,233,343 A | * | 8/1993 | Mazzoni ................. 221/154 |
| 5,242,223 A | | 9/1993 | Koves |
| 5,257,693 A | | 11/1993 | Kwasniak |
| 5,259,668 A | | 11/1993 | Teufel et al. |
| 5,263,596 A | | 11/1993 | Williams |
| 5,267,174 A | | 11/1993 | Kaufman et al. |
| 5,276,810 A | | 1/1994 | Kitamura et al. |
| 5,291,191 A | | 3/1994 | Moore |
| 5,292,029 A | | 3/1994 | Pearson |
| 5,314,243 A | | 5/1994 | McDonald et al. |
| 5,346,297 A | | 9/1994 | Colson, Jr. et al. |
| 5,355,289 A | | 10/1994 | Krenn |
| 5,381,315 A | | 1/1995 | Hamaguchi et al. |
| 5,392,025 A | * | 2/1995 | Figh et al. ................. 340/5.3 |
| 5,392,951 A | | 2/1995 | Gardner et al. |
| 5,408,443 A | | 4/1995 | Weinberger |
| 5,459,648 A | | 10/1995 | Courtney |
| 5,460,294 A | | 10/1995 | Williams |
| 5,502,944 A | | 4/1996 | Kraft et al. |
| 5,537,313 A | | 7/1996 | Pirelli |
| 5,564,803 A | | 10/1996 | McDonald et al. |
| 5,611,051 A | | 3/1997 | Pirelli |
| 5,661,978 A | | 9/1997 | Holmes et al. |
| 5,664,856 A | | 9/1997 | Pacetti |
| 5,671,592 A | | 9/1997 | Yuyama et al. |
| 5,673,983 A | | 10/1997 | Carlson et al. |
| 5,713,485 A | | 2/1998 | Liff et al. |
| 5,720,154 A | | 2/1998 | Lasher et al. |
| RE35,743 E | | 3/1998 | Pearson |
| 5,745,366 A | | 4/1998 | Higham et al. |
| 5,790,409 A | | 8/1998 | Fedor et al. |
| 5,805,455 A | | 9/1998 | Lipps |
| 5,805,456 A | | 9/1998 | Higham et al. |
| 5,842,976 A | | 12/1998 | Williamson |
| 5,852,911 A | | 12/1998 | Yuyama et al. |
| 5,865,745 A | | 2/1999 | Schmitt et al. |
| 5,883,806 A | | 3/1999 | Meador et al. |
| 5,905,446 A | | 5/1999 | Benore et al. |
| 5,905,653 A | | 5/1999 | Higham et al. |
| 5,912,818 A | | 6/1999 | McGrady et al. |
| 5,913,197 A | | 6/1999 | Kameda |
| 5,924,074 A | | 7/1999 | Evans |
| 5,927,540 A | | 7/1999 | Godlewski |
| 5,946,659 A | | 8/1999 | Lancelot et al. |
| 5,971,593 A | | 10/1999 | McGrady |
| 5,997,476 A | | 12/1999 | Brown |
| 6,003,006 A | | 12/1999 | Colella et al. |
| 6,004,020 A | | 12/1999 | Bartur |
| 6,011,999 A | | 1/2000 | Holmes |
| 6,021,392 A | | 2/2000 | Lester et al. |
| 6,032,155 A | | 2/2000 | de la Huerga |
| 6,039,467 A | | 3/2000 | Holmes |
| 6,068,156 A | | 5/2000 | Liff et al. |
| 6,095,985 A | | 8/2000 | Raymond et al. |
| 6,109,774 A | | 8/2000 | Holmes et al. |
| 6,112,502 A | | 9/2000 | Frederick et al. |
| 6,116,461 A | | 9/2000 | Broadfield et al. |
| 6,151,536 A | | 11/2000 | Arnold et al. |
| 6,163,736 A | | 12/2000 | Halfacre |
| 6,163,737 A | | 12/2000 | Fedor et al. |
| 6,170,746 B1 | | 1/2001 | Brook et al. |
| 6,401,991 B1 | * | 6/2002 | Eannone ................. 221/103 |

* cited by examiner

DISPENSING METHOD USING INDIRECT COUPLING

TECHNICAL FIELD

The present invention relates generally to a method for the selective removal of inventoried items.

BACKGROUND ART

This invention relates generally to devices and systems for controlled dispensing of medications, therapeutic agents, or other pharmaceutical items in a hospital environment, nursing home, or the like. More particularly, this invention relates to an improved security or locking system to be used in combination with existing medication dispenser stations and related methods of operation for providing simple but controlled access to any array of pharmaceutical, medical or therapeutic items concurrently with the generation and maintenance of an accurate, detailed access record. Exemplary systems currently available are Pyxis Remote Manager™ and Medstation® both of which are manufactured by Pyxis Corporation and MedSelect® External Lock Modules manufactured by Diebold, Incorporated.

In a hospital environment or the like, a large number of pharmaceutical items such as medications, therapeutic agents, syringes, dressings, etc. are used in the course of individualized medical treatment provided to multiple patients. Such pharmaceutical items are normally stocked at a centralized location such as a hospital pharmacy, nursing stations, or the like for periodic distribution to patients. The distribution of pharmaceutical items is tailored to the specific needs of each nursing station, particularly with respect to the individual medical treatment requirements for patients assigned to each nursing station. For example, many medications are typically prescribed by physicians for administration to specific patients according to a particular time schedule. Other medications and pharmaceutical items are normally stocked at the nursing station for use on an as-needed basis.

At each nursing station, the pharmaceutical items are stored for access by nursing personnel in accordance with individual patient requirements. In this regard, many items are normally maintained in unlocked storage for easy and substantially unrestricted access, while other items such as narcotic medications are normally retained in locked storage to prevent unauthorized access and theft. For all pharmaceutical items, however, withdrawal of pharmaceutical items from inventory is accompanied by updating of the medication administration record (MAR) for the appropriate patient. In this regard, such record maintenance is an important function of nursing personnel to confirm the treatment regimen for each patient, to insure proper charging of patient accounts, and to permit accurate tracking of the pharmaceutical inventory. Unfortunately, due to the exigencies of a typical nursing environment, the medication records are often incomplete and/or inaccurate. As a result, the inventory of some or all of the pharmaceutical items is regularly checked, such as at the conclusion of each nursing shift, in an effort to reduce recording and/or treatment errors and further to minimize pilferage losses.

In recent years, a variety of devices and systems have been proposed in attempts to provide improved inventory control for pharmaceutical items in a hospital environment or the like. Many such devices have contemplated individual medication dispensers located at bedside in association with individual patients. However, the use of multiple bedside dispensers can be relatively costly and further requires regular manual attention to ensure proper loading and individualized programming for each patient. Other systems have envisioned centralized units at a nursing station or the like for maintaining different medications and related pharmaceutical items under locked storage. While such centralized units have provided improved safety and enhanced record keeping for narcotic substances, such units have unduly restricted access to many routine pharmaceutical items. Accordingly, prior centralized medication units have not met with commercial acceptance on any significant scale.

As stated above, there is presently available a wide variety of medication dispenser stations (Pyxis Remote Manager™, Medstation®, MedSelect® External Lock Modules and the like) for use at centralized location in a medical facility. However, one problem with these point-of-use systems is that because the entire system is hard wire (cable) connected, the dispenser station must be located relatively close, if not adjacent, to the refrigerator or drawer to which access is controlled. This limitation proves costly in a hospital environment where space is at a premium. Additionally, there exists the problem of requiring a dispenser station juxtaposed to each and every refrigerator or drawer to which controlled access is desired. Because the manufacturers of these dispenser stations generate income by either selling or leasing such stations, the user is burdened with increased costs.

U.S. Pat. No. 6,151,536, which is incorporated by reference as though fully set forth herein, discloses a method of eliminating the hard wire connection between a dispenser station and a lock of an auxiliary location by using a wireless transmitter or an infra-red coupler. One problem with this method, though, is that it requires the direct coupling of the lock at the auxiliary location to a processor located at the dispensing station. Another problem is that the '536 method requires the user to active manually an item sensor at the dispensing station to record accurately the removal of an inventoried item from the auxiliary location.

U.S. Pat. No. 6,112,502, which is also incorporated by reference as though fully set forth herein, discloses a dispensing method for medical items whereby an existing auxiliary storage location, such as a refrigerator, is retrofitted with a lock module that controls access to the location's contents. The lock module is unlocked via a signal sent from a display terminal or other computer that is directly coupled to the dispensing system. That is, like the '536 method, the '502 method requires a direct coupling between the auxiliary storage location and the central dispensing system. Additionally, the following United States Patents disclose central dispensing systems directly coupled to an auxiliary storage location and are incorporated by reference: U.S. Pat. Nos. 6,068,156; 6,039,467; 5,971,593; 5,912,818; 5,883,806, and 5,790,409. Each of the foregoing patents disclose a central dispensing system that selectively limits access to a directly coupled auxiliary storage location. Because of the direct coupling mechanism, existing dispensing systems cannot control access to locations to which they are not coupled. Naturally, coupling the location to the system results in an unwanted expense.

There exists, therefore, a significant need for an improved security system for controlling access to pharmaceutical, medical, surgical, therapeutic items and the like, wherein there is no need for the dispenser station to be directly coupled to a lock at an auxiliary location, thus allowing existing dispensing systems to remain in place.

The present invention is provided to solve these and other problems.

SUMMARY OF THE INVENTION

The present invention provides a method for selectively dispensing inventoried items. The first step of the method is providing a storage means adapted with a lock. The second step is providing a wireless unlocking means removably secured in the storage means. The wireless unlocking means is able to transmit an unlocking signal upon activation by a user.

The next step of the method is where the user is unlocking the lock in order to access the storage means and the wireless unlocking means. The wireless locking means is wirelessly coupled to a locking system located at a secondary storage location. That is, the lock at the secondary storage location can be lock and unlocked any number of times upon receipt of the unlocking signal. The secondary storage location houses at least one inventoried item. The method further provides for activating the wireless unlocking means to transmit the unlocking signal to the locking system, thereby unlocking the locking system and permitting the user to access the secondary storage location. The method finally provides for removing an inventoried item from the secondary storage location. If desired, the locking system at the secondary location or the lock at the storage means can be relocked and the method repeated.

Further aspects of the invention are disclosed in the detailed description of the preferred embodiment, the drawings and the claims.

BEST MODE FOR CARRYING OUT THE INVENTION

Figure 1:
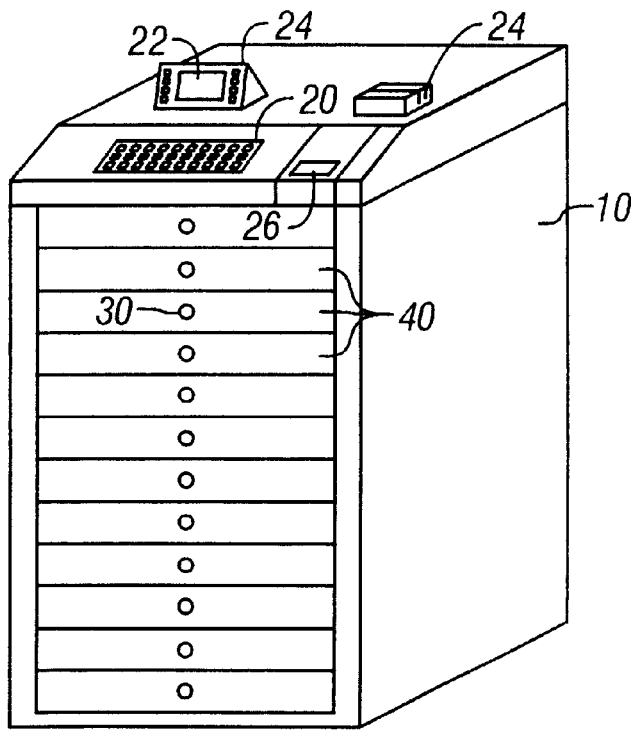
FIG. 1 illustrates one embodiment of a storage means contemplated by the invention.

While this invention is susceptible of embodiments in many different forms, and will herein be described in detail, preferred embodiments of the invention are disclosed with the understanding that the present disclosure is to be considered as exemplifications of the principles of the invention and are not intended to limit the broad aspects of the invention to the embodiments illustrated.

The present invention provides a method for selectively dispensing inventoried items, such as pharmaceutical and therapeutic agents in a hospital. The first step of the method provides a storage means adapted with a lock. In one embodiment, the storage means could be any of the previously described dispenser stations. Other, suitable embodiments include any storage location that can be adapted with a lock such as a drawer, a receptacle, a box, and the like. Of course, the storage means could also include a plurality, or a combination, of any of the foregoing embodiments. The lock can be of any type known in the art, the details of which form no part of the present invention.

In one exemplary method, the storage means has an input means for entering access data, and a lock associated with the input means and capable of being selectively locked and unlocked upon the entry of access data. The input means can be of any known technology such as a keyhole, a alphanumeric keypad, a keyboard, a touch screen, a computer mouse, a coded card reader, a magnetic strip reader, a bar code scanner, a token receptacle, or even biometric-type identification devices such as those that identify a user by fingerprints, hand scans, retina scans, iris scans, voice prints or other body features and the like. In another embodiment of the method, the storage means is associated with a computer processor whereby when a user inputs access data, the processor compares the access data to stored authorized user records to verify that the user is an authorized user. If the user is not so authorized, access to the storage means is denied.

Once the user inputs the access data and, if required, is authorized to access the storage means, the method provides unlocking the lock to the storage means, thereby permitting the user to access the contents of the storage means. According to the method, the storage means selectively limits access to a wireless unlocking means that is removably secured within the storage means. In another embodiment, the wireless unlocking means is permanently secured, tethered, or even integrated into the storage means. The wireless unlocking means is capable of generating or producing an unlocking signal upon activation by the user. In one embodiment, the wireless unlocking means could be programmed to store, indefinitely or for a fixed period of time, any number of predetermined unlocking signals. The form of the unlocking signals could be of any type known in the wireless art such as infrared, radio, electrical, magnetic, and the like.

The method also provides a secondary storage location having a locking system wirelessly coupled to the wireless unlocking means. That is, the locking system is adapted to be locked and/or unlocked upon receipt of the unlocking signal from the wireless unlocking means. The present method contemplates the relocking and reunlocking of the unlocking means. Because of the wireless coupling, the locking system naturally has a sensor for receiving the unlocking signal. In a preferred form of the method, the storage means is not adapted to produce the unlocking signal associated with the locking system of the secondary storage location. The present invention also contemplates that more than one wireless unlocking means may be adapted to produce the unlocking signal, which also contemplates the locking system being adapted to lock and/or unlock after receiving the same or different unlocking signals from a plurality of wireless unlocking means. The locking system could also be adapted to lock and/or unlock after receiving different unlocking signals from a the same wireless unlocking means.

The locking mechanism of the locking system forms no part of the present invention and can be of any type known in the art, including by not limited to: spring-loaded bolt, magnets, pin cylinder, wafer tumbler, cylindrical, lever set, high quality lever, cylinder rim, and the like. Preferably, the locking system can be retrofitted to existing secondary storage locations and may be removably or permanently attached to the secondary storage location. The locking system will also have a power source for its sensor and/or locking mechanism, which may be a direct current, an alternating current, a battery, or a combination thereof. It is also contemplated that the locking mechanism has its own power source, which is activated upon receipt of the unlocking signal, such as those found in an "active" radio frequency transponder. Preferably, the locking system will remain locked in the event that it loses its power source(s) through failure, removal, or otherwise.

In one particular embodiment of the present invention, the locking system has an override system whereby the locking system can be unlocked without activating the unlocking signal from the wireless unlocking means. Preferably, the override system is a manually operated lock and key combination but could be of another embodiment such as those described above, including the described input means. The override system would be used in the event exigent entry into the secondary storage location was necessary, where the locking system lost its power source, or where the user could not locate the wireless unlocking means. In a preferred embodiment, the locking system has a manually operated latch, which is spring-loaded and operates in parallel with the locking system. That is, the latch will cause the locking system to relock without further user activation after it has first been unlocked. Activation of the latch could be adapted to occur after access is gained to the secondary storage location, after a predetermined amount of time, or after manual user activation, and the like. The latch could also comprise part of the override system.

The present invention also provides that the secondary storage location houses at least one inventoried item. The nature of the inventoried item could be any item where an accurate inventory of same is desired, including but not limited to: pharmaceuticals, therapeutic agents, medical agents, drugs, narcotics, medical supplies, machines, equipment, and the like. In a particular embodiment, the storage means is adapted with a recording means to record information associated with the user removing an inventoried item from the secondary storage location, including but not limited to: the access data, the identity of the inventoried item removed, the medium of the inventoried item removed (e.g., a vial, a pill, a premix solution, and the like), the quantity removed, the price, the remaining inventory, the identity of the user, time, date, and the like. More preferably, the recording means would be in communication with an accounting system so that if the method of this invention were used in a hospital, the patient could be accurately charged when an inventoried item was removed and used for his or her benefit. In another embodiment of the invention, the recording means would be coupled to a printing means for the generation of a history report.

Referring to FIG. 1, a storage means is represented by the general reference number 10. The storage means 10 has at least one drawer, or more preferably, a plurality of drawers 40. The storage means 10 has an input means 20 for entering access data, and a lock 30 associated with the input means 20 and capable of being selectively locked and unlocked upon the entry of access data (not shown). According to FIG. 1, the input means 20 is represent by a keyboard, but can by of any known input technology such as a touch screen 22 as part of a display monitor 24, a coded card reader 26, a magnetic strip reader 28, or any other technologies previously described or known in the art.

Figure 2:
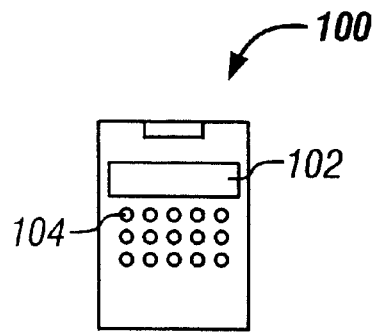
FIG. 2 illustrates one embodiment of the wireless unlocking means contemplated by the present invention.

The present method also provides that the storage means selectively limits access to a wireless unlocking means 100, which is shown in FIG. 2, that is removably secured within the storage means 10. In another embodiment, the wireless unlocking means is permanently secured or even integrated into the storage means (not shown). In a particular embodiment, the wireless unlocking means 100 would be adapted with a display screen 102, which would depict any desired information, including but not limited to: the access data, patient account information, inventory information, and the like. The wireless unlocking means could also be adapted with a keypad 104, which could be coupled with the storage means 10 to allow the entry of supplemental access data to access additional drawers in the plurality 40, or to enter any desired information into the storage means 10 for recording same in the recording means, if so equipped (not shown).

Figure 3:
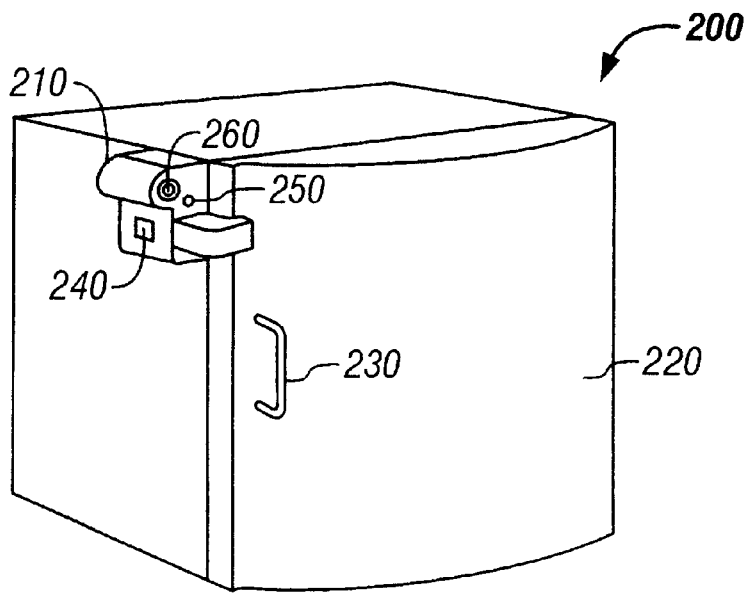
FIG. 3 illustrates one embodiment of an existing refrigerator retrofitted with a locking system.

The wireless unlocking means 100 is wirelessly coupled to the locking system 210 of the secondary storage location 200, which is shown in FIG. 3. The secondary storage location 200 includes a door 220. According to a preferred embodiment, the secondary storage location 200 is a refrigerator of any conventional type equipped to cool its contents below ambient temperature. The door 220 of the secondary storage location 200 is adapted with a handle 230 for easy opening when the locking system 210 is unlocked. The present invention contemplates that the interior area (not shown) of the secondary storage location 200 may be a single storage location in which one or more types inventoried items (not shown) are housed. Alternatively the interior area may be divided into several storage locations. These storage locations may be open storage locations or may be subcompartments to which access is further controlled by electronic or other types of locking mechanisms (not shown).

Access to the interior area is controlled by the unlocking signal (not shown) transmitted by the wireless unlocking means 100. Preferably, the locking system 210, receives the unlocking signal at a sensor 240. The unlocking signal is preferably an infrared wavelength or a radio frequency, depending on whether the user requires line of sight operation. The locking system 210 unlocks when the appropriate unlocking signal is received from the wireless unlocking means 100.

The locking system 210 also includes at least one visual indicator 250, which is preferably an LED type indicator. The visual indicator 250 illuminates when the locking system 210 is unlocked. In alternative embodiments, an additional visual indicator (not shown) would illuminate when the sensor 240 was receiving the unlocking signal from the wireless unlocking means, or when the power source (not shown) of the locking system was operative. In alternative embodiments other types of indicators or additional indicators may be used. Preferably, the power source of the locking mechanism is an alternating current or a battery, or a combination thereof, the strength of which could be depicted on the display screen 102 of the wireless unlocking means. The locking system 210 also includes an override system 260 as part of a manual unlocking mechanism that enables opening the door 220 preferably using a key (not shown). Preferably, a manually operated latch (not shown) operates in parallel with the locking system 210 and causes the locking system 210 to relock without further user activation after it has first been unlocked.

After the locking system 210 receives the appropriate unlocking signal from the wireless unlocking means 100, the locking system unlocks and allows the user to access the contents of the secondary storage location 200, which includes at least one inventoried item (not shown). In one embodiment of the method, the storage means is equipped with a recording means to record the access data the led to the subsequent removal of the inventoried item, as well as the removal itself. The present method contemplates that any information associated with the removal of an inventoried item could be recorded for subsequent retrieval or subsequent incorporation into additional inventory or accounting methods or systems.

While specific embodiments have been illustrated and described, numerous modifications are possible without departing from the spirit of the invention, and the scope of protection is only limited by the scope of the accompanying claims.

I claim:

1. A method for selectively dispensing inventoried items, the method comprising:

providing a storage means adapted with a lock;

providing a wireless unlocking means removably secured in the storage means and capable of transmitting an unlocking signal upon activation by a user;

unlocking the lock, whereby a user can access the storage means and the wireless unlocking means;

providing a secondary storage location having a locking system wirelessly coupled to the wireless unlocking means, the locking system adapted to be selectively unlocked upon receipt of the unlocking signal, and wherein the secondary storage location houses at least one inventoried item;

activating the wireless unlocking means to transmit the unlocking signal to the locking system thereby unlocking the locking system and permitting the user to access the secondary storage location; and removing an inventoried item from the secondary storage location.

2. The method of claim 1 wherein the unlocking signal is a radio frequency or an infrared wavelength.

3. The method of claim 1 wherein the locking system further comprises a power source.

4. The method of claim 3 wherein the power source is an alternating current, a direct current, or a battery.

5. The method of claim 3 wherein if the power source is lost, the locking system remains locked.

6. The method of claim 1 further comprising a plurality of secondary storage locations each having a locking system wirelessly coupled to the wireless unlocking means.

7. The method of claim 1 wherein the secondary storage location is a refrigerator.

8. The method of claim 1 further comprising the step of relocking the locking system.

9. The method of claim 1 wherein the storage means is a drawer.

10. The method of claim 1 wherein the inventoried item is an item selected from the group consisting of pharmaceuticals, therapeutic agents, medical agents, drugs, narcotics, and medical supplies.

11. The method of claim 1 wherein the lock is adapted to be unlocked manually.

12. The method of claim 1 wherein the locking system is adapted to be unlocked manually.

13. A method for selectively dispensing inventoried items, the method comprising:

providing a storage means adapted with a lock;

providing a wireless unlocking means removably secured in the storage means and capable of transmitting an unlocking signal upon activation by a user;

unlocking the lock, whereby a user can access the storage means and the wireless unlocking means;

providing a secondary storage location having a locking system wirelessly coupled to the wireless unlocking means, the locking system adapted to be selectively unlocked upon receipt of the unlocking signal, wherein the storage means is not adapted to produce the unlocking signal, and wherein the secondary storage location houses at least one inventoried item;

activating the wireless unlocking means to transmit an unlocking signal to the locking system thereby unlocking the locking system and permitting the user to access the secondary storage location; and removing an inventoried item from the secondary storage location.

14. A method for selectively dispensing inventoried items, the method comprising:

providing a storage means, the storage means having an input means for entering access data, a lock associated with the input means and capable of being selectively locked and unlocked upon the entry of access data, a recording means capable of recording the access data, and a storage means adapted to the lock;

entering access data into the storage means to unlock the lock and permit a user to access the storage means;

recording the access data;

providing a wireless unlocking means removably secured in the storage means and capable of transmitting an unlocking signal upon activation by the user;

providing a secondary storage location having a locking system wirelessly coupled to the wireless unlocking means, the locking system adapted to be selectively unlocked upon receipt of the unlocking signal, and wherein the secondary storage location houses at least one inventoried item;

activating the wireless unlocking means to transmit an unlocking signal to the locking system thereby unlocking the locking system and permitting the user to access the secondary storage location; and removing an inventoried item from the secondary storage location.

15. A method for selectively dispensing inventoried items, the method comprising:

providing a storage means, the storage means having an input means for entering access data, a lock associated with the input means and capable of being selectively locked and unlocked upon the entry of access data, a recording means capable of recording the access data, and a storage means adapted to the lock;

entering access data into the storage means to unlock the lock and permit a user to access the storage means;

recording the access data;

providing a wireless unlocking means removably secured in the storage means and capable of transmitting an unlocking signal upon activation by the user;

providing a secondary storage location having a locking system wirelessly coupled to the wireless unlocking means, the locking system adapted to be selectively unlocked upon receipt of the unlocking signal, wherein the storage means is not adapted to produce the unlocking signal, and wherein the secondary storage location houses at least one inventoried item;

activating the wireless unlocking means to transmit an unlocking signal to the locking system thereby unlocking the locking system and permitting the user to access the secondary storage location; and removing an inventoried item from the secondary storage location.

16. The method of claim 15 further comprising the step of relocking the locking system.

* * * * *